United States Patent
McGraw et al.

(10) Patent No.: US 7,190,782 B2
(45) Date of Patent: Mar. 13, 2007

(54) PERSONAL COMMUNICATION CENTER PERFORMANCE DISPLAY AND STATUS ALERT SYSTEM

(75) Inventors: Kevin McGraw, Saint John (CA); Richard C. DeGolia, Los Altos, CA (US); Bruce E. Keistead, Saint John (CA)

(73) Assignee: Genesys Telecommunications Laboratories, Inc., Daly City, CA (US)

(*) Notice: Subject to any disclaimer, the term of this patent is extended or adjusted under 35 U.S.C. 154(b) by 0 days.

(21) Appl. No.: 11/386,549

(22) Filed: Mar. 21, 2006

(65) Prior Publication Data

US 2006/0182260 A1    Aug. 17, 2006

Related U.S. Application Data

(63) Continuation of application No. 10/840,527, filed on May 5, 2004, which is a continuation of application No. 09/527,905, filed on Mar. 17, 2000, now Pat. No. 6,748,072.

(51) Int. Cl.
*H04M 3/523* (2006.01)
*G06F 3/048* (2006.01)

(52) U.S. Cl. ............................. 379/265.03; 379/266.1; 715/781; 715/795

(58) Field of Classification Search ............................... 379/265.01–265.08, 266.01, 266.1, 266.02, 379/266.03, 266.06; 715/781, 788, 795
See application file for complete search history.

(56) References Cited

U.S. PATENT DOCUMENTS

| | | | | |
|---|---|---|---|---|
| 5,621,789 A | * | 4/1997 | McCalmont et al. | .. 379/265.06 |
| 5,864,616 A | * | 1/1999 | Hartmeier | ............... 379/265.03 |
| 6,748,072 B1 | | 6/2004 | McGraw et al. | |
| 2004/0208308 A1 | | 10/2004 | McGraw et al. | |

* cited by examiner

*Primary Examiner*—Harry S. Hong
(74) *Attorney, Agent, or Firm*—Donald R. Boys; Central Coast Patent Agency, Inc.

(57) ABSTRACT

In a call center having agent stations including personal computers having video display units (PC/VDUs), connected on a LAN with a server tracking status for call center entities, a system for agent information includes a software application executing on individual PC/VDUs at agent stations. The software application draws on status information from the server and renders the information to the agent using the PC/VDU through output apparatus of the PC/VDU. Rendering may be by text, graphics, or audio, depending on such as conditions and user selection.

15 Claims, 2 Drawing Sheets

PERSONAL COMMUNICATION CENTER PERFORMANCE DISPLAY AND STATUS ALERT SYSTEM

FIELD OF THE INVENTION

The present application is a continuation application of co-pending patent application Ser. No. 10/840,527, filed on May 5, 2004, which is a continuation of patent application Ser. No. 09/527,905 filed on Mar. 17, 2000 and issued as U.S. Pat. No. 6,748,072 on Jun. 8, 2004, which are incorporated herein in their entirety by reference.

BACKGROUND OF THE INVENTION

The field of telecommunications has grown significantly with the advent of computer-integrated-telephony (CTI) and more recently, data-network-telephony (DNT). Contributions to both of these technologies have led to the advent of multimedia communications centers capable of handling a wide variety of communication types and mediums.

A large customer-care center serves as a good example of a telecommunications center that may be dedicated to serving a very large customer base through constant communication using state-of the-art techniques aided by intelligent software applications running on processors connected to the centers telecommunication system.

A communication center of the type described in this specification typically employs a plurality of agents whom have been trained to operate communication equipment and applications for the dedicated purpose of serving customers who call into the center.

A multimedia communication center enhanced with DNT capability as known to the inventor will include, along with a connection-oriented-switched-telephony (COST) system, an Internet protocol (IP) telephony system for handling communication events sourced from a data-packet-network (DPN), which, in many cases, is the well-known Internet network. It will be appreciated by one with skill in the art that agent responsibilities in such a system are expanded over those of a traditional or conventional call-in center to include working with e-mails, video mails, IP voice calls, computer-aided chat sessions, and other computer/network aided communication mediums.

In such a multimedia center agents are typically located at workstations adapted with equipment and network connections that are suitable for communication in both a COST and DNT environment. For example, each agent station typically comprises a telephone connected to a central COST routing system and a personal computer with a video display unit (PC/VDU), which is connected to a local-area-network LAN. The LAN is further connected to an IP routing system and agents receive IP calls routed to them over the LAN to their PC/VDU's. In some cases, DNT capable telephones are also incorporated such that they may be switched from COST mode to DNT mode and back again.

In addition to enhanced equipment utilized at agent level, other equipment is provided for the purpose of automated interface with customers calling into the system at network level. Such equipment includes interactive voice response (IVR) systems, which may be adapted for both COST and DNT communication. In systems known to the inventor, intelligent routing is available at levels above the agent level (internal routing system).

CTI software known to the inventor as T-Server software is provided to run on processors implemented at switches and terminals existing in COST, and in some instances, DPN network levels for the purpose of providing intelligent routing routines to be executed at network level. These CTI processors are interconnected with a separate DPN such that routing commands may be communicated between instances of T-Servers. Moreover, additional data may be obtained about a caller at network level and passed to agent level over the separate data network, often ahead of a routed communication event.

Extending intelligent routing capability into networks allows performance of agent level routing from within a network. These routing rules are, of course, adapted to communication center capability. For example, statistical call routing, predictive call routing, skill-based routing, priority routing and other routines known to the inventor may be utilized at network level.

With all of the advanced routing and communication capabilities available in the art, communication center managers and supervisors must continually motivate agents working in the center along with managing agent function in accordance with the agent's designated duties. One of the traditional tools used for this purpose is known in the art as a communication center display board sometimes referred to as a signboard.

A communication-center display board is a computerized display system that is hung or mounted in a centrally visible location within a communication center for the purpose of providing call-load status, call event alerts, motivational messages, and any other information that managers deem pertinent to agent function and performance. A good example of a communication-center display board existing in prior art is the NetBrite™ display system provided by SYMON™.

The NetBrite™ system comprises a network-connected, full matrix, light-emitting-diode (LED) display board that may be configured for the type of data that is to be displayed to agents. The system has an internal sound card and speaker system including software for playing WAV, MIDI and other audio files as well as steaming audio. The system may be configured to a number of differing modes such as flashing data, scrolling data, page-through data, and audible alerting. Moreover, the physical display interface may be configured to display a plurality of separate addressable sections for individualizing portions of the display for an agent or group of agents.

Display systems like the one described in the example above are network-connected and receive data directly from a data server or servers providing the status and performance information for communication center activity. The system uses standard network data wiring and connection means for interface and integration to a communication center LAN system enhanced typically with transfer control protocol/Internet protocol (TCP/IP) capability.

One obvious problem associated with a display system of this type is that it is shared by many communication center agents who must devote a significant amount of attention to the system throughout their workday. Diverting attention to the common or shared system may take away from or delay other agent duties. Another drawback with a common or shared system is that the volume level must be loud enough for all agents to hear. In some cases, this fact may distract some agents engaged in audible communication with customers. Still another problem is that the display characteristic is limited to a compact set of abstractly metered data, which an agent must read to understand and act upon.

What is clearly needed is a communication center status reporting and warning system that may be distributed to and executed from individual agent stations such that an agent need not devote primary attention to a shared system. Such a system could be configured to use graphical images as well as audible conventions for data provision and would allow a system-trained agent to quickly grasp communication center status and alert states without diverting the agent from other duties.

SUMMARY OF THE INVENTION

In a preferred embodiment of the present invention, in a call center having agent stations each having a personal computer with a video display unit (PC/VDU), a system for informing agents of call center-related status is provided, comprising a server tracking call center activities and calculating status for individual call center entities, the server connected on a network in the call center; and an agent-informing application executing on individual ones of the PC/VDUs at agent stations, the PC/VDUs at the agent stations also connected on the network. The system is characterized in that the application draws on status data from the server and provides status information to an agent using an individual PC/VDU through output apparatus of the individual PC/VDU.

In some embodiments status includes status and warnings related to transaction queues to which the agent using a PC/VDU is related. The software may provide graphic displays indicating call center status information, audio renditions through a speaker associated with the PC/VDU used by the agent, or combinations thereof. Audio may be played over call conversations at a level not interrupting the conversations.

In another aspect of the invention a software application for use with a personal computer having a video display unit (PC/VDU) at an agent station in a call center is provided, comprising an access module for drawing status information from a server connected on a common network with the PC/VDU; and a rendition module for rendering the status information through output apparatus of the PC/VU for an agent using the PC/VDU.

In a preferred embodiment rendition is by graphic and text display on the video display monitor of the PC/VDU. Rendition may also be by audio rendition through a speaker associated with the PC/VDU used by the agent, and audio may be provided over telephone conversations engaged in by the agent. The status information includes status and warnings related to transaction queues to which the agent using a PC/VDU is related.

In another aspect of the invention, in a call center having agent stations each having a personal computer with a video display unit (PC/VDU), a method for informing agents of call center-related status is provided, comprising steps of (a) drawing status information by a software application executing on an individual (PC/VDU) from a server commonly connected on a communication network with the PC/VDU at the agent station; and (b) rendering the information to an agent using the PC/VDU through output apparatus of the PC/VDU.

In preferred embodiments of the method, in step (a), status includes status and warnings related to transaction queues to which the agent using a PC/VDU is related. Also in preferred call center status information may be provided to an agent by audio rendition through a speaker associated with the PC/VDU used by the agent, or by text and graphic displays, or in combination. The audio-rendered information may be rendered over telephony call audio as an agent converses with a caller, at a whisper lever.

In embodiments of the present invention, taught in enabling detail below, for the first time a system is provided for informing agents of status information in a call center, wherein information and its presentation may be tailored to individual agents, and provided in a manner to avoid disturbing other agents, or distracting the receiving agents attention from other tasks.

BRIEF DESCRIPTION OF THE DRAWING FIGURES

DESCRIPTION OF THE PREFERRED EMBODIMENTS

According to a preferred embodiment of the present invention, a personalized communication-center performance and warning system is provided as a distributed software application adapted to run at each agent workstation within the center.

Figure 1:
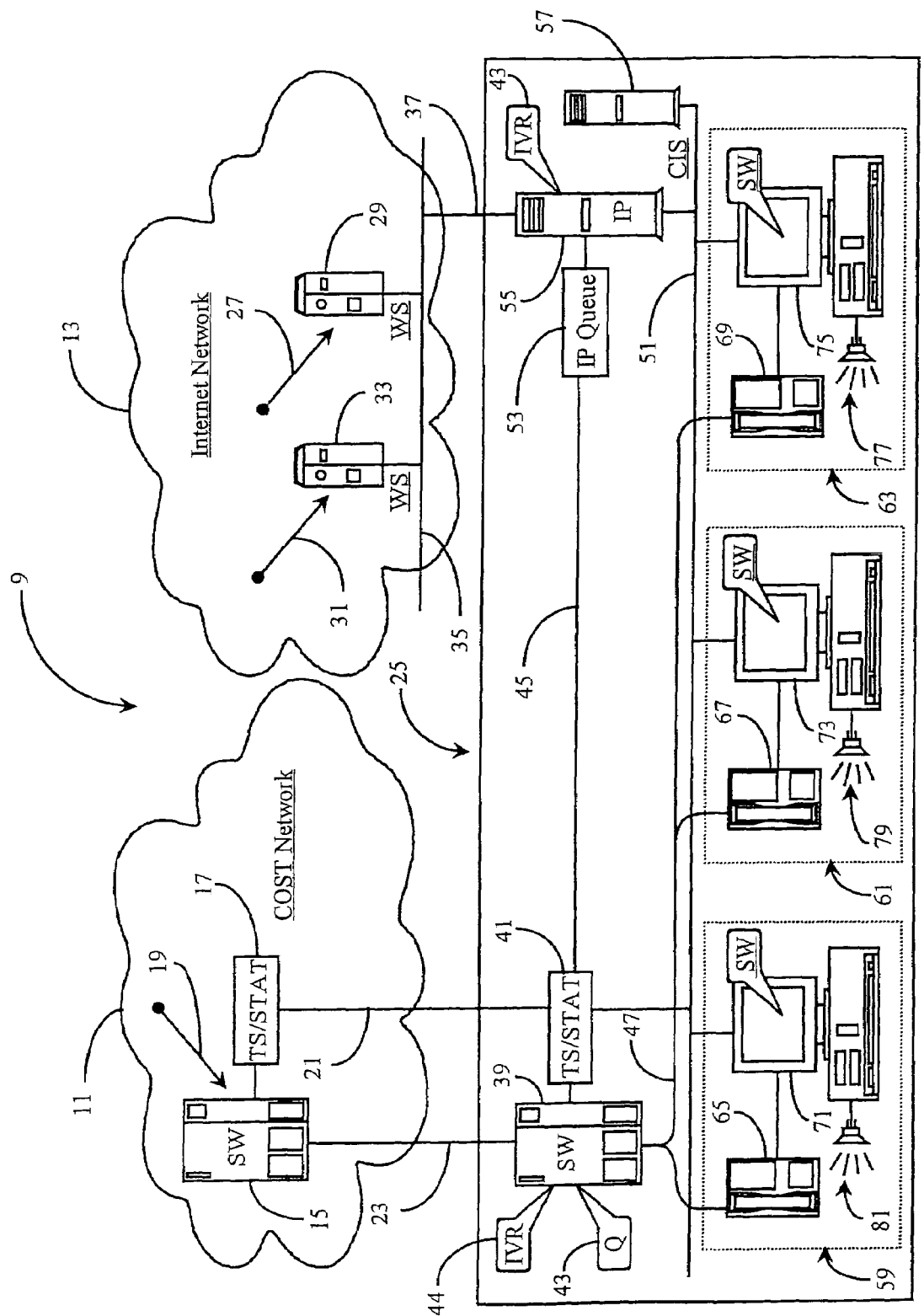
FIG. 1 is an overview of a dual-capable communication center utilizing a communication-center performance display and warning system according to an embodiment of the present invention.

FIG. 1 is an overview of a dually-capable communication center 25 utilizing a communication-center performance display and warning system (SW) according to an embodiment of the present invention. A communication network 9 is illustrated as a preferred network embodiment for practicing the present invention. Network 9 comprises a connection oriented switched telephony (COST) network 11 (conventional telephone network), a data packet network (DPN) 13 (such as the Internet), and communication center 25.

COST network 11 may be any type of switched telephony network public or private in nature. In a preferred embodiment, COST 11 is a well-known public switched telephony network (PSTN). The inventor chooses the PSTN network as a preferred COST network because of its high public-access characteristic.

DPN 13 may be-any type of wide-area-network (WAN) public or private in nature, operating as a shared bandwidth, data-packet network. In a preferred embodiment, DPN 13 is the well-known Internet network and will hereinafter be referred to as Internet 13. The inventor chooses the Internet network because of its high public-access characteristic. The invention, however, is not limited to the Internet.

Communication center 25 is a dually-capable center meaning that it is capable of handling both COST and DNT communication. Communication center 25 may be a small or large corporate center serving as a central location for customer service. In typical application, center 25 communicates with customers calling in from COST network 11 or initiating communication events from Internet 13. It is important to note here that the method of practicing the present invention is not limited to a dually-capable center as illustrated in the example, but may be practiced in either a COST only center or a DNT only center separately.

Communication network 9 demonstrates the state of the art in network communication and communication-center service. All of the communication capability and routing functionality mentioned in the background section may be assumed to be present in this example.

COST network 11 comprises a telephony switch 15 enhanced by a CTI processor 17 running an instance of T-Server 17. T-Server 17 is a CTI application known to the inventor that is adapted to provide intelligent control over switch 15 for such as call routing purposes. Switch 15 may be any type of telephony switch known in the art and capable of processing calls. Processor 17 is connected to switch 15 by a CTI link. Other functional equipment known in the art such as a service control point (SCP) in the network, network access points, network bridges, as well as other telephony switches may be assumed to be present within COST network 11.

Switch 15 is connected to a telephony switch 39 within communication center 25 by a telephony trunk 23. Switch 39 functions as a central switch adapted for routing incoming calls within communication center 25. Switch 39 is enhanced by a processor 41 running an instance of T-Server. Processor 41 is connected to processor 17, within network 11, by a digital data network (DDN) 21 separate from trunk lines over which telephone calls are established. DDN 21 and connected processors 17 and 41 provide an effective means for enabling communication-center control over switch 15 in network 11. T-Server provides intelligent routing determination for incoming calls and DDN 21 allows added data about callers to be forwarded to center 25, often ahead of an arriving COST call.

A COST call, represented herein by a vector labeled 19, may arrive at switch 15 from anywhere in network 11, or from another network through a network bridge. At switch 15, interaction may be initiated with the caller and additional data about the caller may be obtained. An ultimate agent-level destination may be determined for call 19 while it is stationed in switch 15. It is assumed in this example, that call 19 is destined for center 25 and therefore, will be routed to switch 39 over trunk 23. Additional data about call 19 is passed over DDN 21. The data and call routing determination is matched such that the data and call 19 are routed to the appropriate agent within center 25.

Center 25 has a plurality of manned agent-workstations provided therein for the purpose of enabling optimum service to customers. These are represented by workstations 59, 61, and 63. It will be appreciated that there will be many more workstations provided in a very large communication center, however, the illustration of three stations in this example is deemed adequate for explanation of the present invention.

Agent station 59 comprises an agent telephone 65 and a personal computer with a video display unit (PC/VDU) 71. Agent telephone 65 is connected to central switch 39 by COST wiring 47. PC/VDU 71 is connected to a local area network (LAN) 51, which is adapted, in this embodiment, for transfer control protocol/Internet protocol (TCP/IP).

Although it is not required to practice the present invention, agent workstations 61 and 63 are illustrated as having identical equipment and connections as station 59. For example, agent telephones 67 (workstation 61) and 69 (workstation 63) are connected to switch 39 by internal wiring 47. Agent PC/VDU's 73 (station 61) and 75 (station 63) are connected to LAN 51. The inventor illustrates identical capabilities for simplicity in illustration only. It is not to be construed as a limitation.

Agent telephones 65–69 are chiefly adapted for COST communication as exemplified by COST wiring 47, which connects them to switch 39 as previously described. However, telephones 65–69 may also be used as DNT-capable telephones as illustrated by data connections to respective PC/VDU's in each station 59–63. In some cases, telephones 65–69 may be adapted for either COST only or DNT only communication.

PC/VDU's 71–75 are adapted for DNT communication by virtue of their connections to LAN 51 and installed IP-telephony software. Because LAN 51 is Internet enabled, agents operating PC/VDU's 71–75 may deal with all manner of IP communication arriving at center 25 from Internet 13.

Internet 13 has an Internet backbone 35 illustrated therein and intended to represent the many lines, connection points, and equipment types making up the Internet network as a whole. In this example, two WEB-servers (WS) 33 and 29 are illustrated as connected to backbone 35. WEB-servers 33 and 29 represent well-known file servers adapted to serve electronic WEB pages to those accessing the servers from remote appliances through Internet connection. Servers 33 and 29 are, in this example, hosted by the enterprise hosting communication center 25. Servers 33 and 29 contain WEB pages that provide contact means and information to Internet visitors who desire contact with an agent working in center 25.

Communication center 25 has an IP router 55 provided therein and adapted to receive IP calls from Internet 13. IP calls are represented as a vector 31 entering WEB server 33, and as a vector 27 entering WEB server 29. Calls 31 and 27 may represent any of the DNT communication means mentioned in the background section. IP telephone calls, e-mail, video calls, represent but a few of the possibilities. IP calls 31 and 27 are initiated at servers 33 and 29 respectively by customer initiation of appropriate interactive means provided in a given WEB page accessed by the customer.

IP calls are routed over backbone 35 to a network-connection line 37 that ultimately connects to IP router 55 held within center 25. Connection line 37 is, in this example, an Internet capable data line. IP router 55 is connected to LAN 51. IP calls 31 and 29 are routed over LAN 51 to appropriate LAN connected terminals.

A customer information system (CIS) server 57 is provided within center 25 and is connected to LAN 51. CIS server 57 is adapted to store and server any data about known customers that may be useful to agents communicating with them. Data held in CIS 57 may include but is not limited to customer account information, personal transaction histories, address and contact information, and so on.

Other systems adapted to aid agents in interacting with customers are also available within communication center 25, and in some cases, within networks 11 and 13. For example, switch 39 is illustrated as having an interactive voice response (IVR) system 44. IVR 44 is adapted to interact with COST callers on an agent's behalf when required by enterprise rules. A queue (Q) system 43 is also available at switch 39 as is generally known in the art. Queue system 43 may be a first-in-first-out (FIFO) queue, or it may be an enhanced queue with enhancement provided by CTI processor 41. DNT equivalents are provided at IP router 55 and represented by an IP queue 53 and an IVR system 43. Such conventions are used to aid in handling call flow within communication center 25. A data link 45 connecting queue 53 to processor 41 provides T-Server enhancement to queue 53 as well as IVR 43 and IP router 55. In this way, all call events may be handled by one integrated set of communication center rules.

As described in the background section, traditional communication signboards adapted to notify agents of certain communication-center call states and other information are prone to divert agent's responsibilities from tasks at hand by virtue of their centralized location within a center. Therefore, the inventor provides a distributed software application illustrated herein as (SW) to run in the background at each agent workstation 71, 73, and 75.

Distributed instances of SW are adapted to function as personalized information systems for the agents and are capable of visual as well as audible modes of information processing. Each distributed instance of information SW is configured to periodically check communication-center data sources for applicable information based on that particular station's configuration.

To further illustrate, consider an example wherein all three illustrated instances of information SW (one at each of stations 71–77) are identically configured to retrieve the same information as it becomes available from data sources. In this case, an applicable data source is, for example, processor 41, which is adapted (among other functions) to serve T-Server data to requesting nodes. T-Server data may include communication-center call-load status, agent call performance data, percentages of required out-bound calls per agent, total number of calls in queue, average call handling time statistics, and any other applicable information that may be deemed by the enterprise hosting center 25 to be applicable for agent dissemination.

SW distributed at each of stations 71–75 periodically checks data. sources, such as processor 41, over LAN 51 for the most current data available. In some cases, each distributed SW instance is time-configured to request data simultaneously such that all agents are privy to the same data at the same time. In other cases, the data is picked up at different times by different stations if required. Similarly, the distributed applications may be somewhat personalized to a particular agent's station and a current agent's duties.

If for example, an agent at station 63 is only answering DNT communication, then SW at station 75 might be configured to communicate the number of calls in queue 53, but not the number of calls in queue 43 and so on. If the agent switches to answering only COST calls, then SW at station 75 may detect the switch and change request protocol accordingly such that now only data about COST queue 43 is available.

In most instances, much of the same data will be applicable to all active agents and may help to direct an agent's responsibilities in some respects. SW of the present invention utilizes pre-recorded WAV or other audible files for conveying informative states to agents. The system utilizes the internal PC speaker at each workstation 71–75 to play audible files as is illustrated by speaker icons 81–77, or alternatively may utilize additional speaker or speakers installed and operable at the agent station. In this way, an agent may control the volume to a low level (or whisper) so that other individual agents are not distracted. Audible files played to agents may indicate many of the types of available data that would otherwise be displayed on a signboard perhaps in numeric format.

In addition to an ability to play audio files, SW of the present invention also enables visual display of communication-center data through the use of animated figures or graphics that flash or move across a PC monitor screen. Each different figure or icon may represent a different set of data. Moreover, SW of the present invention may also be configured to provide a standard signboard display having all of the metered data displayed thereon in numeric, text, and/or symbol form. There are many possibilities in alternative embodiments.

Figure 2:
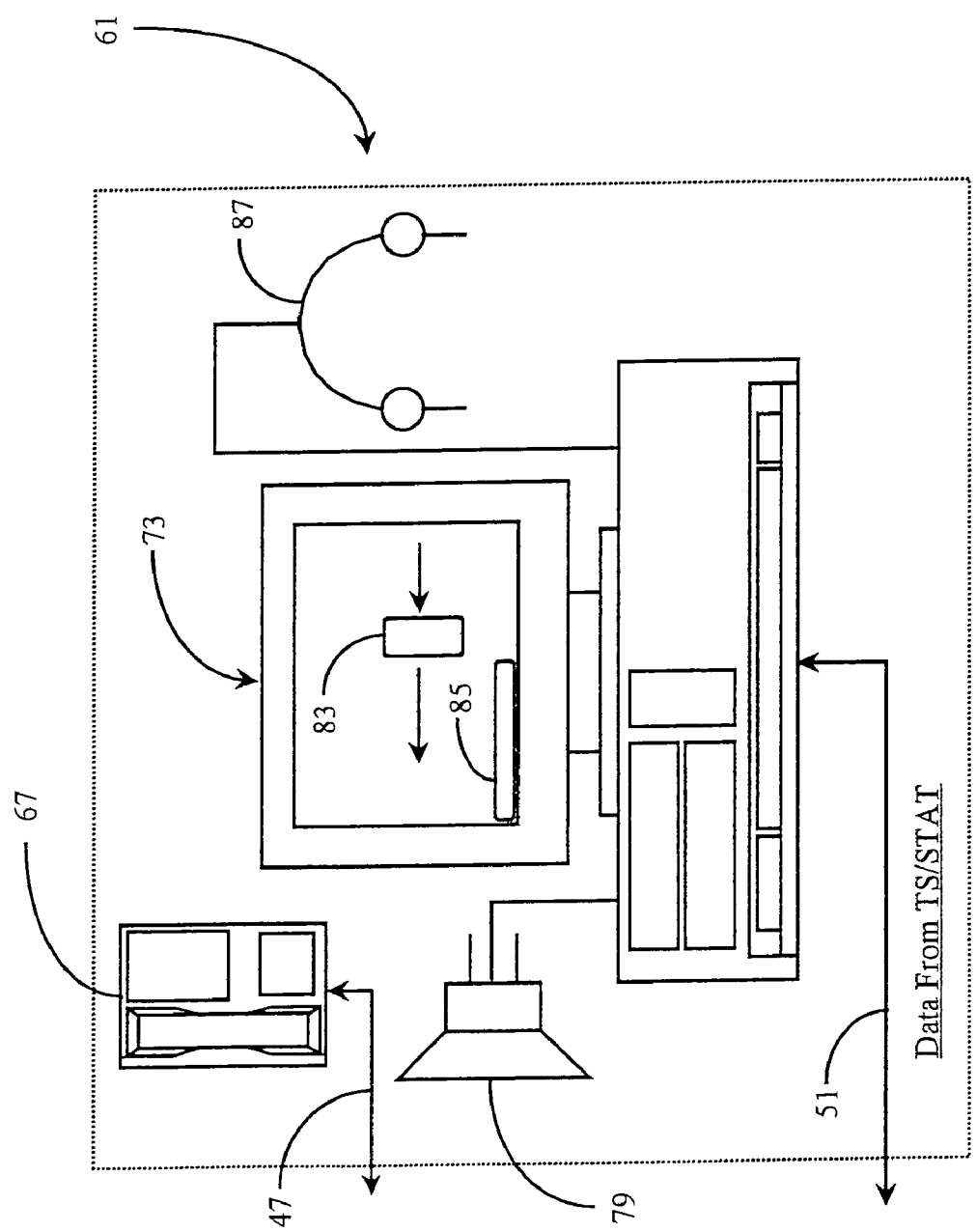
FIG. 2 is a block diagram of an agent workstation adapted with the communication center performance display and warning system of FIG. 1.

FIG. 2 is a block diagram of agent workstation 61 adapted with the communication center performance display and warning system of FIG. 1. The SW of the present invention of which an instance is represented on each of stations 71–75 of FIG. 1 is represented in this example as elements 83 and 85. Element 83 represents a graphics icon or animated figure moving in the display screen of PC 73. Movement of element 83 is represented by the directional arrows showing movement from right to left in this example.

It is important to note here, that element 83 may represent any conceivable graphic illustration that may be used to equate to a "state" existing in communication center 25. For example, a man pushing a full wheel barrel and laboring across the screen may indicate a full call-waiting queue. A superman figure with an agent's name emblazoned across his jersey may indicate the center's current top-performing agent. The possibilities are limited only by the imagination.

Element 85 represents a legible signboard that is minimized to the available task bar area of the screen. Element 85 may be maximized to occupy a full screen and may serve as a real time interface for communication center data. The data may appear in any conventional form such as text data, symbols representing data, numeric data, or a combination thereof. When the displayed board is minimized, the data that would normally be viewable may be expressed audibly with generated WAV files. For example, a WAV file may be used to express the number of calls currently waiting in queue. There could be a pre-recorded version of the file such as "the number of calls in queue for department 10 is now" and a parsing technique and synthesized voice addition could fill in the current number as indicated at the data source to complete the sentence. Call-load thresholds and other real-time data may be expressed in similar fashion.

Other data such as statistical information, averages, number of disconnects, and the like may also be expressed audibly. Speaker 79, which in actual implementation is an internal PC speaker in this example, may be controlled in volume by the application such that audible alerts do not interfere with other audible communication engaged in by an agent. In some embodiments, all of the agent's internal speakers may be set to a specific volume decided upon by a supervisor or manager.

In still another embodiment, the "whisper capability" of the internal speaker may be extended to an agent's headset, represented herein as element number 87, such that the agent may still hear audible system information while engaged with a customer on a telephone call.

The SW of the present invention is, in a preferred embodiment, configurable to individual agents and or groups of agents. This is preferred because of a fact that in a large communication center it is common to have separate groups of agents that are responsible for different types of communication and levels of customer service. There may be separate queues set up for these agents. Statistics regarding the performance of different groups of agents as well as call-load statistics about calls directed to the separate groups may vary widely. Therefore, individually configurable instances of SW provide a means for getting the right information to the right group of agents.

In yet other embodiments, managers and supervisors may have instances of SW on their stations that are configured to obtain certain parts of data from a number of different groups for monitoring purposes. Such an instance of SW would report, for example, the numbers of completed calls per hour from sales, finance, service, and technical support. There are many possibilities. Moreover, distributed instances of SW may be upgraded to new versions and new capabilities over the network from a remote location or by a knowledge worker within center 25.

It will be apparent to one with skill in the art that the method and apparatus of the present invention is not limited to practice in a conventional customer care center wherein all agents are LAN-connected and operating in a centralized location. The method and apparatus of the present invention may also be practiced on a WAN wherein agents occupy stations that are remote from each other as long as there is a central data source such as a server connected to the WAN to supply the desired data to remotely distributed applications.

It will also be apparent to one with skill in the art that the software of the present invention may make full use of media capabilities and display options supported by current platforms and display systems without departing from the spirit and scope of the present invention. For example, instead of distributed applications residing at independent and fully functional workstations, the SW may be centrally executed and extended to such as "dumb" display terminals having only enough memory to support distributed display interfaces.

The method and apparatus of the present invention should be afforded the broadest scope under examination. The method and apparatus of the present invention should be limited only by the claims that follow.

What is claimed is:

1. In a call center having agent stations each having a computer appliance with a display, a system for informing agents of call center-related status, comprising:
   a server tracking call center activities and calculating status for individual call center entities, the server connected on a network in the call center; and
   an agent-informing application executing on individual ones of the computer appliances at agent stations, the computer appliances at the agent stations also connected on the network;
   characterized in that the application draws on status data from the server and provides status information to an agent using an individual computer appliance through a window on the display of the individual computer appliances, wherein when the application window is maximized on the display, the status information is conveyed visually to the agent and when the window is minimized the status information is conveyed to the agent via audio rendition.

2. The system of claim 1 wherein status includes status and warnings related to transaction queues to which the agent using a computer appliance is related.

3. The system of claim 1 wherein the software provides graphic displays indicating call center status information.

4. The system of claim 1 wherein call center status information is provided to an agent by audio rendition through a speaker associated with the used by the agent.

5. The system of claim 4 wherein the audio-rendered information is rendered over telephony call audio as an agent converses with a caller, at a whisper level.

6. A software application for use with a computer appliance with a display at an agent station in a call center, comprising:
   an access module for drawing status information from a server connected on a common network with the computer appliance; and
   a rendition module for rendering the status information through an application window on the display of the computer appliance for an agent using the computer appliance, wherein when the application window is maximized on the display, the status information is conveyed visually to the agent and when the window is minimized the status information is conveyed to the agent via audio rendition.

7. The software application of claim 6 wherein rendition is by graphic and text display on the video display monitor of the computer appliance.

8. The software application of claim 6 wherein the status information includes status and warnings related to transaction queues to which the agent using a computer appliance is related.

9. The software application of claim 6 wherein the status information is provided to an agent by audio rendition through a speaker associated with the computer appliance used by the agent.

10. The software application of claim 9 wherein the audio-rendered information is rendered over telephony call audio as an agent converses with a caller, at a whisper level.

11. In a call center having agent stations each having a computer appliance with a display, a method for informing agents of call center-related status, comprising steps of:
   (a) drawing status information by a software application executing on an individual computer appliance from a server commonly connected on a communication network with the computer appliance at the agent station; and
   (b) rendering the information to an agent using the computer appliance through an application window on the display of the computer appliance, wherein when the application window is maximized on the display, the status information is conveyed visually to the agent and when the window is minimized the status information is conveyed to the agent via audio rendition.

12. The method of claim 11 wherein, in step (a), status includes status and warnings related to transaction queues to which the agent using a computer appliance is related.

13. The method of claim 11 wherein, in step (b), the software provides graphic displays indicating call center status information.

14. The method of claim 11 wherein, in step (b), call center status information is provided to an agent by audio rendition through a speaker associated with the computer appliance used by the agent.

15. The method of claim 14 wherein the audio-rendered information is rendered over telephony call audio as an agent converses with a caller, at a whisper level.

* * * * *

UNITED STATES PATENT AND TRADEMARK OFFICE
CERTIFICATE OF CORRECTION

| | | |
|---|---|---|
| PATENT NO. | : 7,190,782 B2 | |
| APPLICATION NO. | : 11/386549 | |
| DATED | : March 13, 2007 | |
| INVENTOR(S) | : Kevin McGraw et al. | |

It is certified that error appears in the above-identified patent and that said Letters Patent is hereby corrected as shown below:

On the Title Page,

Item (75) Inventors, line 3          Delete "Keistead"

Insert -- Kierstead --

Signed and Sealed this
Third Day of February, 2015

Michelle K. Lee
*Deputy Director of the United States Patent and Trademark Office*